(12) United States Patent
Lee et al.

(10) Patent No.: US 8,283,117 B2
(45) Date of Patent: Oct. 9, 2012

(54) DISEASE DIAGNOSIS METHOD, MARKER SCREENING METHOD AND MARKER USING TOF-SIMS

(75) Inventors: Tae Geol Lee, Daejeon (KR); Dae Won Moon, Daejeon (KR); Byong Chul Yoo, Goyang-si (KR); In Hoo Kim, Goyang-si (KR)

(73) Assignee: Korea Research Institute of Standards and Science, Daejeon (KR)

( * ) Notice: Subject to any disclaimer, the term of this patent is extended or adjusted under 35 U.S.C. 154(b) by 81 days.

(21) Appl. No.: 12/994,263

(22) PCT Filed: Jun. 25, 2008

(86) PCT No.: PCT/KR2008/003620
§ 371 (c)(1),
(2), (4) Date: Nov. 23, 2010

(87) PCT Pub. No.: WO2009/145382
PCT Pub. Date: Dec. 3, 2009

(65) Prior Publication Data
US 2011/0095179 A1    Apr. 28, 2011

(30) Foreign Application Priority Data
May 26, 2008    (KR) .......................... 10-2008-0048552

(51) Int. Cl.
*A61K 38/21*    (2006.01)
(52) U.S. Cl. .............. 435/6; 435/32; 436/111; 436/128; 514/115; 514/117
(58) Field of Classification Search ............... 435/6, 7.1, 435/29, 32; 436/71, 95, 98, 111, 128, 129; 514/115, 117, 177, 274, 283
See application file for complete search history.

(56) References Cited

U.S. PATENT DOCUMENTS

| 2005/0014165 A1 | 1/2005 | Lee et al. |
| 2007/0280444 A1 | 12/2007 | Granzer et al. |
| 2008/0118462 A1* | 5/2008 | Alani et al. ................. 424/85.2 |
| 2009/0258848 A1* | 10/2009 | Chakravarti et al. .......... 514/177 |

FOREIGN PATENT DOCUMENTS

| KR | 1020080003472 A | 1/2008 |
| WO | 0004149 A2 | 1/2000 |
| WO | 0125784 A1 | 4/2001 |
| WO | 2007098432 A2 | 8/2007 |

* cited by examiner

*Primary Examiner* — Kiet T Nguyen
(74) *Attorney, Agent, or Firm* — The Webb Law Firm

(57) ABSTRACT

The present invention relates to a disease diagnosis method, a marker screening method, and a marker using a time-of-flight secondary ion mass spectrometry (TOF-SIMS), and more particularly, to a large intestine cancer diagnosis method, a large intestine cancer marker screening method, and a large intestine cancer marker using a time-of-flight secondary ion mass spectrometry (TOF-SIMS). Specifically, the present invention provides a method diagnosing a disease using a pattern of secondary ion mass (m/z) peaks of biological samples measured using a time-of- flight secondary ion mass spectrometry (TOF-SIMS) as a marker, a marker screening method being a reference judging an existence or non-existence of a disease, and a marker configured of specific secondary ion mass peaks.

8 Claims, 13 Drawing Sheets

Figure 1

| Control | Sex | Age year | WBC 10³/μl | Hb g/dL | CEA ng/ml | Control | Sex | Age year | WBC 10³/μl | Hb g/dL | CEA ng/ml | Control | Sex | Age year | WBC 10³/μl | Hb g/dL | CEA ng/ml | Control | Sex | Age year | WBC 10³/μl | Hb g/dL | CEA ng/ml |
|---|---|---|---|---|---|---|---|---|---|---|---|---|---|---|---|---|---|---|---|---|---|---|---|
| N-1 | M | 35 | 5.59 | 16.2 | 2.5 | N-21 | M | 44 | 4.24 | 16.1 | 0.9 | N-41 | M | 61 | 5.49 | 18 | 2 | N-61 | M | 43 | 5.59 | 16 | 2.7 |
| N-2 | F | 53 | 4.09 | 13.3 | 0.7 | N-22 | M | 44 | 3.53 | 15.8 | 1.4 | N-42 | M | 47 | 4.41 | 15.1 | 1.5 | N-62 | M | 49 | 5.24 | 15.2 | 1.2 |
| N-3 | F | 44 | 3.48 | 12.7 | 0.5 | N-23 | F | 45 | 7.22 | 12.9 | 1.5 | N-43 | M | 48 | 7.05 | 14.3 | 1.2 | N-63 | F | 52 | 5.02 | 12.6 | 2.3 |
| N-4 | M | 49 | 4.66 | 15.8 | 0.9 | N-24 | M | 44 | 5.24 | 16.1 | 1.1 | N-44 | F | 46 | 3.81 | 12.7 | 2.1 | N-64 | F | 38 | 6.03 | 11 | 0.7 |
| N-5 | F | 46 | 3.8 | 10.9 | 2.1 | N-25 | M | 48 | 5.05 | 14.9 | 1.9 | N-45 | M | 51 | 6.67 | 16.8 | 2.6 | N-65 | M | 57 | 5.85 | 15.6 | 1.4 |
| N-6 | M | 55 | 7.08 | 17.5 | 2.1 | N-26 | F | 41 | 3.45 | 14.3 | 2.5 | N-46 | M | 62 | 11.12 | 16.5 | 1.5 | N-66 | F | 45 | 5.8 | 12 | 1 |
| N-7 | M | 60 | 4.63 | 14.5 | 1.8 | N-27 | F | 41 | 6.02 | 16.5 | 3.9 | N-47 | M | 48 | 6.67 | 16.8 | 2.6 | N-67 | F | 54 | 4.94 | 15.8 | 2 |
| N-8 | F | 56 | 4.88 | 12.7 | 1.3 | N-28 | F | 34 | 8.84 | 13.3 | 1.3 | N-48 | M | 49 | 4.2 | 17.6 | 1.8 | N-68 | F | 59 | 4.34 | 14 | 1.3 |
| N-9 | M | 43 | 7.24 | 16.2 | 2.3 | N-29 | M | 49 | 4.21 | 16.3 | 2.7 | N-49 | F | 48 | 4.1 | 13 | 1 | N-69 | F | 41 | 5.81 | 14.8 | 2.1 |
| N-10 | M | 56 | 4.93 | 15.4 | 1.1 | N-30 | M | 44 | 5.1 | 16.1 | 2.2 | N-50 | F | 53 | 4.94 | 12.2 | 2.2 | N-70 | F | 64 | 4.72 | 12.5 | 1.4 |
| N-11 | F | 49 | 4.41 | 13.2 | 1.2 | N-31 | F | 53 | 4.81 | 13.2 | 1 | N-51 | F | 37 | 7.37 | 13.4 | 1.3 | N-71 | M | 48 | 4.52 | 15.2 | 1 |
| N-12 | M | 45 | 4.13 | 15.7 | 0.5 | N-32 | M | 56 | 4.37 | 15.8 | 1.4 | N-52 | M | 58 | 5.79 | 14.8 | 5 | N-72 | F | 56 | 5.57 | 16.2 | 2.6 |
| N-13 | F | 38 | 6.02 | 13 | 1.5 | N-33 | F | 53 | 3.05 | 13.6 | 0.8 | N-53 | M | 58 | 4.04 | 16.1 | 1 | N-73 | F | 38 | 5.88 | 14.7 | 0.6 |
| N-14 | F | 57 | 4.46 | 13.8 | 1.2 | N-34 | F | 51 | 4.81 | 13.5 | 2.5 | N-54 | M | 43 | 7.88 | 13.2 | 1.5 | N-74 | M | 50 | 4.13 | 13.2 | 1.3 |
| N-15 | M | 35 | 5.23 | 14.1 | 2 | N-35 | M | 59 | 4.86 | 15.7 | 2 | N-55 | F | 45 | 5.71 | 14.7 | 0.9 | | | | | | |
| N-16 | M | 44 | 5.56 | 13.9 | 2.6 | N-36 | M | 39 | 5.17 | 16.4 | 0.8 | N-56 | F | 40 | 5.23 | 13.1 | 0.8 | | | | | | |
| N-17 | F | 58 | 4.85 | 13.9 | 2.6 | N-37 | F | 48 | 4.13 | 12.9 | 0.9 | N-57 | F | 53 | 4.34 | 15.3 | 5.8 | | | | | | |
| N-18 | M | 58 | 4.68 | 14.1 | 1.7 | N-38 | M | 47 | 6.99 | 16 | 1 | N-58 | F | 54 | 4.84 | 12.8 | 3 | | | | | | |
| N-19 | F | 40 | 4.1 | 13.3 | 1.6 | N-39 | M | 65 | 6.08 | 14.7 | 3.4 | N-59 | M | 64 | 5.2 | 15.5 | 1.4 | | | | | | |
| N-20 | M | 40 | 7.18 | 15.9 | 2.1 | N-40 | M | 46 | 3.93 | 14 | 3.2 | N-60 | M | 69 | 7.17 | 17.2 | 2.2 | | | | | | |

No abnormalities were found in all normal controls during colonoscopy.

Figure 2

| Patient | Sex | Age year | WBC 10³/μl | Hb g/dL | CEA ng/ml | Location of tumor | Preop CRT | Stage T | Stage N | Stage M | Cell Type | Differentiation[a] | Tumor Size cm | vl[b] | ALI[c] | PNI[d] |
|---|---|---|---|---|---|---|---|---|---|---|---|---|---|---|---|---|
| C-1 | M | 68 | 4.32 | 14.4 | 23.6 | Rectum | Yes | - | - | 0 | Adenocacinoma | 2 | - | - | - | - |
| C-2 | F | 71 | 9.00 | 9.4 | 66.9 | A- & T-colon cancer | No | 3 | 2 | 1 | Adenocacinoma | 2 | 8 | No | 1 | 2 |
| C-3 | M | 72 | 10.66 | 11.4 | 9.3 | A-colon & Rectal cancer | No | - | - | 1 | Adenocacinoma | 2 | - | - | - | - |
| C-4 | M | 51 | 3.72 | 14.0 | 2.1 | Rectum | Yes | 2 | 1 | 0 | Adenocacinoma | 2 | 2 | No | 1 | 2 |
| C-5 | F | 52 | 6.00 | 13.6 | 2.4 | Rectal cancer | Yes | 4 | 2 | 1 | Mucinous cacinoma | - | 4.1 | Yes | 1 | 1 |
| C-6 | F | 32 | 3.31 | 11.3 | 0.9 | Rectal cancer | Yes | 3 | 1 | 0 | Adenocacinoma | 2 | 3.2 | No | 1 | 2 |
| C-7 | M | 68 | 7.44 | 12.6 | 1.3 | Sigmoid colon | No | 3 | 1 | 0 | Adenocacinoma | 2 | 3.5 | No | 2 | 2 |
| C-8 | F | 66 | 5.97 | 12.0 | 1.7 | Transverse colon | No | 3 | 2 | 0 | Adenocacinoma | 2 | 2.5 | Yes | 1 | 2 |
| C-9 | F | 78 | 8.09 | 11.5 | 34.6 | T-colon cancer | No | 3 | 0 | 0 | Adenocacinoma | 1 | 10 | No | 1 | 2 |
| C-10 | F | 55 | 5.44 | 13.1 | 3.4 | Rectal cancer | Yes | 3 | 1 | 0 | Adenocacinoma | 2 | 0.2 | No | 2 | 2 |
| C-11 | F | 63 | 9.38 | 11.1 | 4.9 | A-colon cancer | No | 3 | 0 | 0 | Adenocacinoma | 2 | 7 | No | 2 | 2 |
| C-12 | F | 58 | 5.49 | 11.3 | 1.8 | T-colon cancer | No | 4 | 1 | 0 | Mucinous cacinoma | - | 3.5 | No | 1 | 2 |
| C-13 | F | 64 | 5.11 | 12.9 | 10.2 | S-colon cancer | No | 3 | 2 | 0 | Adenocacinoma | 2 | 3.6 | Yes | 1 | 1 |
| C-14 | M | 44 | 3.67 | 12.2 | 4.3 | Rectal cancer | Yes | 0 | 0 | 0 | Adenocacinoma | 2 | - | - | - | - |
| C-15 | F | 73 | 5.11 | 11.8 | 2.9 | S-colon cancer | No | 3 | 1 | 0 | Adenocacinoma | 2 | 5 | Yes | 2 | 2 |
| C-16 | M | 49 | 7.93 | 14.0 | 2.7 | D-colon cancer | No | 4 | 0 | 0 | Adenocacinoma | 2 | 6 | Yes | 2 | 2 |
| C-17 | F | 52 | 2.67 | 12.7 | 2.8 | Rectal cancer | Yes | 3 | 1 | 0 | Mucinous cacinoma | 4 | 1.1 | No | 2 | 2 |
| C-18 | M | 61 | 3.26 | 12.0 | 2.7 | Rectal cancer | Yes | 3 | 0 | 0 | Adenocacinoma | 2 | 3.8 | No | 2 | 2 |
| C-19 | F | 57 | 7.61 | 12.1 | 12.0 | HF colon cancer | No | 4 | 1 | 0 | Adenocacinoma | 2 | - | - | - | - |
| C-20 | M | 57 | 4.64 | 14.7 | 4.1 | S-colon cancer | No | 4 | 2 | 0 | Adenocacinoma | 1 | 3.5 | Yes | 1 | 2 |
| C-21 | M | 57 | 4.24 | 13.6 | 5.7 | S-colon cancer | No | 3 | 1 | 0 | Adenocacinoma | 2 | 3.1 | No | 2 | 2 |
| C-22 | M | 62 | 10.35 | 16.7 | 2.3 | Rectal cancer | No | 1 | 0 | 0 | Adenocacinoma | 2 | 1.3 | Yes | 1 | 2 |
| C-23 | M | 52 | 5.86 | 12.5 | 2.4 | Rectal cancer | No | 3 | - | 1 | Adenocacinoma | 3 | 2.5 | No | 2 | 2 |
| C-24 | M | 60 | 4.77 | 11.1 | 21.1 | Rectal cancer | Yes | 3 | 0 | 0 | Adenocacinoma | 2 | 3.6 | No | 2 | 2 |
| C-25 | M | 44 | 8.02 | 16.5 | 3.6 | S-colon cancer | No | 3 | 0 | 0 | Adenocacinoma | 2 | 6 | No | 1 | 2 |
| C-26 | M | 43 | 4.42 | 13.2 | 3.1 | Rectal cancer | No | 3 | 0 | 0 | Adenocacinoma | 2 | 2 | Yes | 2 | 2 |
| C-27 | F | 75 | 6.32 | 12.5 | 1.5 | RSJ colon cancer | No | 3 | 0 | 0 | Adenocacinoma | 1 | 2.4 | No | 1 | - |
| C-28 | M | 65 | 5.93 | 12.0 | 24.0 | Cecal cancer | No | 4 | 2 | 0 | Adenocacinoma | - | 4 | - | - | 2 |
| C-29 | M | 45 | 6.87 | 14.0 | 8.3 | A-colon cancer | No | 3 | 2 | 0 | Mucinous cacinoma | 2 | 7.5 | No | 2 | 2 |
| C-30 | M | 51 | 3.45 | 15.8 | 27.1 | Rectal cancer | Yes | 3 | 0 | 0 | Adenocacinoma | 1 | 2.5 | No | 1 | 2 |
| C-31 | M | 54 | 5.51 | 14.2 | 2.8 | RSJ colon cancer | No | 3 | 0 | 0 | Adenocacinoma | 2 | 3 | No | 2 | 2 |
| C-32 | F | 54 | 3.41 | 11.5 | 2.4 | Rectal cancer | Yes | 3 | 1 | 0 | Adenocacinoma | 2 | - | - | - | - |
| C-33 | F | 40 | 4.26 | 12.1 | 1.3 | Rectal cancer | Yes | 3 | 2 | 0 | Adenocacinoma | 3 | 6.5 | No | 2 | 2 |
| C-34 | M | 57 | 7.18 | 13.0 | 8.9 | Rectal cancer | No | 3 | 1 | 1 | Adenocacinoma | 2 | - | - | - | - |
| C-35 | M | 60 | 5.58 | 12.9 | 85.1 | Rectal cancer | No | 3 | 2 | 1 | Adenocacinoma | 2 | 8 | Yes | 1 | 2 |
| C-36 | M | 77 | 5.21 | 12.6 | 2.0 | S-colon cancer | No | 3 | 0 | 0 | Adenocacinoma | 1 | 5.5 | No | 1 | 2 |
| C-37 | M | 49 | 6.55 | 13.1 | 1.6 | D-colon cancer | No | 3 | 0 | 0 | Adenocacinoma | 2 | 8 | No | 1 | 2 |
| C-38 | M | 36 | 4.96 | 13.1 | 52.5 | Rectal cancer | Yes | 3 | 1 | 0 | Adenocacinoma | 1 | 2 | No | 2 | 2 |
| C-39 | F | 60 | 2.87 | 12.3 | 1.9 | Rectal cancer | Yes | 2 | 0 | 0 | Adenocacinoma | 2 | 1.5 | No | 2 | 2 |
| C-40 | F | 52 | 10.54 | 8.6 | 7.4 | T-colon cancer | No | 4 | 1 | 1 | Adenocacinoma | 2 | 11 | Yes | 1 | - |
| C-41 | M | 41 | 6.56 | 10.9 | 0.5 | A-colon cancer | No | 3 | 2 | 0 | Adenocacinoma | 2 | 8 | No | 1 | 2 |
| C-42 | M | 55 | 5.26 | 13.7 | 1.2 | Rectal cancer | No | 2 | 0 | 0 | Adenocacinoma | 1 | 2.5 | No | 1 | 2 |
| C-43 | M | 26 | 7.35 | 11.1 | 4.4 | D-colon cancer | No | 3 | 1 | 0 | Adenocacinoma | 2 | 4.3 | No | 2 | 2 |
| C-44 | F | 45 | 9.33 | 12.9 | 3.0 | S-colon cancer | No | 3 | 0 | 0 | Adenocacinoma | 1 | 3.5 | No | 2 | 2 |
| C-45 | M | 72 | 5.45 | 9.9 | 2.9 | A- & S-colon cancer | No | 4 | 1 | 0 | Mucinous cacinoma | 4 | 10 | No | 1 | 2 |
| C-46 | F | 61 | 3.99 | 10.5 | 4.3 | Rectal cancer | Yes | 2 | 0 | 0 | Adenocacinoma | 2 | 2 | No | 2 | 2 |
| C-47 | M | 65 | 5.76 | 11.2 | 3.9 | Rectal cancer | Yes | 0 | 1 | 0 | Adenocacinoma | 3 | - | - | - | - |

Figure 3

| Patient | Sex | Age year | WBC 10³/μl | Hb g/dL | CEA ng/ml | Location of tumor | Preop CRT | Stage T | Stage N | Stage M | Cell Type | Differentiation[a] | Tumor Size cm | vi[b] | ALI[c] | PNI[d] |
|---|---|---|---|---|---|---|---|---|---|---|---|---|---|---|---|---|
| C-48 | M | 48 | 5.98 | 16.2 | 1.2 | Rectal cancer | No | 2 | 1 | 0 | Adenocarcinoma | 2 | 3.2 | No | 1 | 2 |
| C-49 | M | 45 | 6.87 | 14.0 | 8.3 | A-colon cancer | No | 4 | 2 | 0 | Mucinous cacinoma | 4 | 7.5 | No | 1 | 2 |
| C-50 | F | 70 | 4.05 | 11.4 | 2.1 | Rectal cancer | Yes | 2 | 0 | 0 | Adenocarcinoma | 1 | 4.8 | No | 2 | 2 |
| C-51 | M | 45 | 3.40 | 13.9 | 4.1 | Rectal cancer | Yes | 3 | 1 | 0 | Adenocarcinoma | 2 | 3.2 | Yes | 2 | 2 |
| C-52 | M | 59 | 5.72 | 12.3 | 1.3 | Rectal cancer | No | 4 | 2 | 1 | Adenocarcinoma | 2 | 6 | No | 1 | 2 |
| C-53 | F | 80 | 2.87 | 12.3 | 1.9 | Rectal cancer | Yes | 2 | 1 | 0 | Adenocarcinoma | 2 | 1.5 | No | 2 | 2 |
| C-54 | M | 40 | 5.20 | 13.4 | 1.8 | Rectal cancer | No | 2 | 0 | 0 | Adenocarcinoma | 1 | 1.3 | Yes | 2 | 2 |
| C-55 | M | 80 | 5.18 | 13.4 | 2.2 | Rectal cancer | Yes | 2 | 0 | 0 | Adenocarcinoma | 2 | 0.5 | No | 2 | 2 |
| C-56 | M | 55 | 6.08 | 12.9 | 1.7 | Rectal cancer | Yes | 2 | 0 | 0 | Adenocarcinoma | 2 | 1.3 | No | 2 | 2 |
| C-57 | M | 66 | 3.94 | 14.3 | 0.6 | S-colon cancer | No | 3 | 1 | 0 | Adenocarcinoma | 2 | 3 | No | 2 | 2 |
| C-58 | F | 58 | 7.69 | 13.0 | 6.9 | A-colon cancer | No | 3 | 0 | 0 | Adenocarcinoma | 2 | 1.5 | No | 2 | 2 |
| C-59 | M | 41 | 5.72 | 14.2 | 0.6 | S-colon cancer | No | 1 | 1 | 0 | Adenocarcinoma | 2 | - | - | - | - |
| C-60 | M | 62 | 3.76 | 13.9 | 1.4 | S-colon cancer | No | 2 | 0 | 0 | Adenocarcinoma | 2 | 2.3 | No | 1 | 2 |
| C-61 | F | 71 | 3.27 | 12.4 | 13.8 | RSJ colon cancer | No | 3 | 0 | 0 | Adenocarcinoma | 1 | 7.3 | No | 2 | 2 |
| C-62 | M | 44 | 3.79 | 13.1 | 4.6 | Rectal cancer | Yes | 2 | 0 | 0 | Adenocarcinoma | 2 | 3.5 | No | 2 | 2 |
| C-63 | F | 47 | 6.39 | 11.9 | 1.3 | S-colon cancer | No | 4 | 2 | 0 | Adenocarcinoma | 2 | 3.5 | No | 1 | 2 |
| C-64 | F | 32 | 2.69 | 11.8 | 1.1 | Rectal cancer | Yes | 4 | 0 | 0 | Adenocarcinoma | 2 | 3 | No | 2 | 2 |
| C-65 | M | 24 | 7.87 | 13.4 | 24.1 | S-colon cancer | No | 3 | 2 | 1 | Mucinous cacinoma | 4 | - | - | - | - |
| C-66 | F | 57 | 9.73 | 11.1 | 1.5 | A-colon cancer | No | 3 | 0 | 0 | Adenocarcinoma | 3 | 10 | No | 1 | 2 |
| C-67 | M | 58 | 4.20 | 13.2 | 6.9 | Rectal cancer | Yes | 3 | 0 | 0 | Adenocarcinoma | 1 | 2 | No | 2 | 2 | a: Differentiation of Adenocarcinoma, 1 - Well Differentiation, 2 - Moderated Differentiation, 3 - Poorly Differentiation, 4 - Mucinous or Signet Ring Cell Type b: Venous Invasion c: Angiolymphatic Invasion -: Missing data

| Control | Prediction[a] | | | Patient | Prediction[a] | | |
|---|---|---|---|---|---|---|---|
| | ToF-SIMS | | FOBT[b] | | ToF-SIMS | | FOBT[b] |
| | Total Intensity | CH$_3^*$ | | | Total Intensity | CH$_3^*$ | |
| N-21 | N | N | N | C-21 | C | C | C (687) |
| N-22 | N | N | N | C-22 | C | C | C (1489) |
| N-23 | N | N | N | C-23 | C | C | N |
| N-24 | N | N | N | C-24 | C | C | C (2446) |
| N-25 | N | N | N | C-25 | C | C | C (2013) |
| N-26 | N | N | N | C-26 | C | C | N |
| N-27 | N | N | N | C-27 | C | C | C (1543) |
| N-28 | N | N | N | C-28 | N | N | C (954) |
| N-29 | N | N | N | C-29 | N | N | C (1752) |
| N-30 | N | N | N | C-30 | C | C | N |
| N-31 | N | C | N | C-31 | C | C | C (616) |
| N-32 | N | N | N | C-32 | C | C | C (1601) |
| N-33 | C | N | N | C-33 | C | C | N |
| N-34 | N | N | N | C-34 | C | C | C (502) |
| N-35 | N | N | N | C-35 | C | C | C (1183) |
| N-36 | N | N | N | C-36 | C | C | C (1556) |
| N-37 | N | N | N | C-30 | C | C | C (>2000) |
| N-38 | C | C | N | C-31 | C | C | C (389) |
| N-39 | C | C | N | C-32 | C | C | N |
| N-40 | N | N | N | C-33 | C | C | N |
| N-41 | N | N | N | C-34 | C | C | N |
| N-42 | C | C | N | C-35 | C | C | C (>2000) |
| N-43 | N | N | N | C-36 | C | C | C (447) |
| N-44 | N | N | N | C-37 | C | C | C (321) |
| N-45 | N | C | N | C-38 | C | C | C (120) |
| N-46 | N | N | N | C-39 | C | C | C (1523) |
| N-47 | N | N | N | C-40 | C | C | C (1560) |
| N-48 | N | N | N | C-48 | C | C | N |
| N-49 | N | N | N | C-49 | C | C | C (1752) |
| N-50 | C | N | N | C-50 | C | C | C (1883) |
| N-51 | N | N | N | C-51 | C | C | C (432) |
| N-52 | N | N | N | C-52 | C | C | C (2017) |
| N-53 | N | N | N | C-53 | C | C | N |
| N-54 | C | C | N | C-54 | C | C | N |
| N-55 | C | N | N | C-55 | C | C | C (157) |
| N-56 | N | N | N | C-56 | C | C | C (>2000) |
| N-57 | N | N | N | C-57 | C | C | N |
| N-58 | N | N | N | C-58 | C | C | N |
| N-59 | N | N | N | C-59 | N | C | N |
| N-60 | C | C | N | C-60 | C | N | N |
| N-61 | C | C | N | C-61 | C | C | C (>2000) |
| N-62 | C | N | N | C-62 | C | C | C (>2000) |
| N-63 | N | N | N | C-63 | C | C | C (514) |
| N-64 | C | C | N | C-64 | C | C | N |
| N-65 | N | C | N | C-65 | C | C | C (1623) |
| N-66 | N | N | N | C-66 | C | C | N |
| N-67 | N | N | N | C-67 | C | C | N |
| N-68 | C | C | N | | | | |
| N-69 | N | N | N | | | | |
| N-70 | N | N | N | | | | |
| N-71 | N | N | N | | | | |
| N-72 | N | N | N | | | | |
| N-73 | N | N | N | | | | |
| N-74 | N | N | N | | | | | a: N and C are for normal and colorectal cancer, respectively.

b: The FOBT employed in our present study did not require any dietary restrictions, and the analytical cut off for the FOBT positive was 100 ng Hb/ml. The number in the blanket indicates total amount of Hb (ng) per 1 ml volume stool.

DISEASE DIAGNOSIS METHOD, MARKER SCREENING METHOD AND MARKER USING TOF-SIMS

TECHNICAL FIELD

The present invention relates to a disease diagnosis method, a marker screening method, and a marker using a time-of-flight secondary ion mass spectrometry (TOF-SIMS), and more particularly, to a large intestine cancer diagnosis method, a large intestine cancer marker screening method, and a large intestine cancer marker using a time-of-flight secondary ion mass spectrometry (TOF-SIMS). A marker used for detecting a specific disease can be extracted according to the marker screening method of the present invention and the disease can be diagnosed by the extracted marker. The marker and the diagnosis method according to the present invention can be used for the first medical examination, a prognosis, and a disease monitoring, etc.

BACKGROUND ART

A cancer, which is a disease interrupting a function of normal cells due to immortalized cells, includes a lung cancer, a stomach cancer, a breast cancer, a large intestine cancer, etc., but can substantially be caused in all tissues.

The early cancer diagnosis is based on an external change of a biological tissue according to a growth of cancer cells.

In recent, however, a diagnosis and a detection of cancer have been attempted using a very small amount of biomolecules existing in a cell or a biological tissue, such as DNA, etc. (Korea Publication Patent No. 2008-0003472, International Publication Patent No. 2000-004149, U.S. Publication Patent 2004-586856, U.S. Publication Patent 2003-690880).

However, the most commonly used cancer diagnosis method may include a diagnosis using a tissue sample obtained through a biopsy or a diagnosis using images. However, the biopsy has disadvantages of giving patients an acute pain and incurring high costs as well as consuming much time until the diagnosis.

Also, in the case where patients actually develops cancer, there is a risk of inducing metastasis of cancer during the biopsy process and in the case of a region not capable of obtaining the tissue sample through the biopsy, the biopsy has a disadvantage in that the disease cannot be diagnosed until the doubted tissue is extracted through a surgical operation.

The diagnosis using images judges a cancer based on images obtained through X-ray, nuclear magnetic resonance imaging method using a contrast medium attached with disease target substance, nuclear imaging, etc. However, the diagnosis using the images has disadvantages in that it is a large possibility of a misdiagnosis according to a skill level of an operator or a reader and largely depends on precision of equipment obtaining an image.

Furthermore, since even the most precision equipment cannot detect a tumor of several mm or less, the diagnosis using the images has a disadvantage in that it is difficult to detect the tumor in the first stage of a disease. Also, since to obtain images, patients or persons who can have a disease is exposed to an electromagnetic wave inducing genomic mutation, the diagnosis using the images has disadvantages of an induction of another disease and a limitation of the frequency of the diagnosis through the images.

Whether a cancer of a digestive system is a disease or not is usually judged by observing its images with the naked eye using an endoscope; however, the process gives patients an acute pain and even though an abnormal symptom is found by observing the images with the naked eye, to accurately judge the diseases of a malignant/benign tumor, a polyp, etc., the biopsy must necessarily be performed. In particular, the large intestine cancer is a commonplace cancer within the third place in view of attack rate around the World and its curability largely depends on a progress stage of cancer.

In particular, when the large intestine cancer is found in the first stage through the early diagnosis, it has a very high cure rate. Therefore, above all thing, it is important to early find the large intestine cancer by the accurate early diagnosis, however, an abnormal symptom accompanied according to the progress of the cancer is insignificant. In most cases, it is common that the disease is recognized by a color change in excrements due to bleeding and although patients or persons who can have the disease are tested, it is common to observe the disease through the endoscope. Therefore, to accurately judge the disease, the biopsy must necessarily be performed.

DISCLOSURE

Technical Problem

To solve the aforementioned problems, an object of the present invention provides a method capable of rapidly, simply, and inexpensively diagnosing a disease with a non-invasive method without giving patients a pain, a marker screening method being a reference of this diagnosis, and a marker capable of judging the existence or non-existence of a disease.

More specifically, the present invention provides a disease diagnosis method and a marker screening method using a time-of-flight secondary ion mass spectrometry (TOF-SIMS).

To solve the aforementioned problems, another object of the present invention provides to a large intestine cancer diagnosis method, a large intestine cancer marker screening method, and a specific secondary ion mass group being a detection reference of large intestine cancer using a time-of-flight secondary ion mass spectrometry (TOF-SIMS).

Technical Solution

A disease diagnosis method according to the present invention diagnoses a disease, as a marker, using a pattern of secondary ion mass (m/z) peaks of biological samples measured using a time-of-flight-mass spectrometry (TOF-MS), the TOF-MS being preferably a time-of-flight secondary ion mass spectrometry (TOF-SIMS).

At this time, the pattern being the marker is a pattern that the secondary ion mass (m/z) is in a region of 1 to 500.

This is because an object or a composition thereof, such as a protein, a gene, a metabolite capable of obtaining information on a disease can be analyzed in this region.

Therefore, the existence or non-existence of peaks and the change or unchanged of intensity in a region where the position of the secondary ion mass (m/z) is preferably 1 to 500, more preferably 1 to 300 are a reference of disease judgment.

At this time, the biological samples may include excrements; urine; tears; salvia; external discharge of skin, respiratory tract, enteric tract, and digestive tract; plasma; serum; blood; spinal fluid; lymph; body fluid; tissue; tissue homogenate; portion of tissue; cell; cell extract; or in vitro cell culture.

The pattern used to diagnose the disease is configured of the positions of the secondary ion mass (m/z) peaks, the intensity of the peaks or a combination thereof obtained by measuring the biological samples by the time-of-flight secondary ion mass spectrometry, wherein the existence or non-existence of the peaks and the change or unchanged of the intensity at the position of the specific secondary ion mass (m/z) in the pattern are a reference of disease judgment.

To increase the accuracy and reliability of the diagnosis, it is preferable that the disease diagnosis method performs a diagnosis by the change in the positions of the secondary ion mass peaks, the change in the intensity of the secondary ion mass peaks, the extinction of the secondary ion mass peaks, the generation of the secondary ion mass peaks, or a combination thereof by comparing at least one reference pattern selected from a normal pattern being a pattern configured of the secondary ion mass peaks of the biological samples of persons not having a specific disease and a disease patterns being patterns configured of the secondary ion mass peaks of the biological samples of patients having a specific disease with an object pattern being a pattern configured of the secondary ion mass peaks of the biological samples of persons who can have the specific disease.

The reference pattern may be the normal pattern or the disease pattern. At this time, the normal pattern may be obtained by statistically processing the secondary ion mass pattern of at least one person that does not have the disease and the disease pattern be obtained by statistically processing the secondary ion mass pattern of at least one person having specific disease.

Preferably, each of the normal pattern, the disease pattern, and the object pattern is a pattern of the same secondary ion mass region in a region of 1 to 500 and is measured under the measurement conditions of the same time-of-flight secondary ion mass spectrometry conditions. Each of the normal pattern, the disease pattern, and the object pattern may be normalized with total accumulated intensity or an average of total accumulated intensity of the region (m/z region configuring the pattern) of the secondary ion mass peaks and may be normalized with the intensity of the specific peak or the average of the intensity of the specific peak, such as $CH_3^+$.

To perform the more effective time-of-flight secondary ion mass spectrometry, the biological samples may be biological samples subjected to a typical preprocessing to facilitate secondary ionization and to have low surface roughness. However, the preprocessing, which is to obtain the effective secondary ion peaks likewise the measurement conditions of the time-of-flight secondary ion mass spectrometry, has little effect on the positions or the relative intensity (intensity of each normalized peaks) of the peaks and therefore, the disease diagnosis method according to the present invention is not limited to the measurement conditions of the time-of-flight secondary ion mass spectrometry conditions or the preprocessing of the sample.

Also, to minimize the effects of the measurement conditions of the time-of-flight secondary ion mass spectrometry or the preprocessing conditions of the biological samples, preferably, the secondary ion mass patterns of the biological samples of persons not having a disease, a patient, persons who can have a specific disease are measured under the same measurement conditions of the time-of-flight secondary ion mass spectrometry and the same preprocessing conditions of the biological samples to compare the reference pattern with the object pattern, thereby diagnosing the disease by the change in the positions of the peaks, the change in the intensity of the peaks, the extinction of the peaks, the generation of the peaks, or a combination thereof.

The normal pattern and the disease pattern configuring the reference pattern can be obtained by a typical statistical processing and a similar level of the reference pattern and the object pattern can usually be performed by a typical statistical algorithm.

Preferably, the specific disease being the diagnosis object is the large intestine cancer and the biological samples are excrements or excremental liquid. Preferably, the excremental liquid is obtained by stirring excrements and buffer solution including phosphate buffered saline (PBS) and then separating the liquid.

In the case where the disease is the large intestine cancer, in comparing the reference pattern and the object pattern, preferably, the comparison object (the pattern being the marker) for the disease diagnosis is at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0.

More preferably, the pattern is configured of at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass.

Most preferably, the pattern is configured of at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass normalized with the total accumulated intensity detected in the region where the secondary ion mass (m/z) is 1 to 500 or the intensity of the specific peak, such as $CH_3^+$.

The patterns being the marker are the normal pattern; the disease patter; or the normal pattern and the disease pattern;.

When the normal pattern or the disease pattern is obtained by statistically processing the detection results of the plurality of secondary ion masses, the normalization is performed by the average of the total accumulated intensity detected in the region where the secondary ion mass (m/z) is 1 to 500 or the average of the intensity of the specific peak, such as $CH_3^+$.

At this time, ones (including the intensity of noise level) having secondary ion not being detected in at least one secondary ion mass selected from the group of secondary ion masses of 81.0, 83.0, 125.9, 126.9, 131.9, 140.9, 141.9, 148.9, 157.9, 158.9, 205.1, 217.0, 222.9, and 233.0 are also a meaningful pattern.

In the case of judging the disease by selecting a plurality of secondary ion masses selected from the group of secondary ion masses of 81.0, 83.0, 125.9, 126.9, 131.9, 140.9, 141.9, 148.9, 157.9, 158.9, 205.1, 217.0, 222.9, and 233.0, preferably, the disease is judged by statistical detection tendency at the positions of the plurality of secondary ion masses selected from the group of secondary ion masses configured of 14 secondary ion masses (m/z). At this case, the detection tendency means the generation of the peaks, the extinction of the peaks, the increase in the intensity of the peaks, or the degradation in the intensity of the peaks.

A marker screening method using a TOF-SIMS according to the present invention comprises the steps of: a) obtaining a normal pattern being a pattern configured of secondary ion mass (m/z) peaks of biological samples of persons not having a specific disease; b) obtaining a disease pattern being a pattern configured of secondary ion mass (m/z) peaks of biological samples of patients having a specific disease; and c) extracting a marker of a specific disease by comparing the difference in the normal pattern and the disease pattern.

Preferably, the step c) extracts at least one secondary ion mass (m/z) selected from a group of the position changed, intensity changed, extinct, and generated peaks by comparing the normal pattern and the disease pattern and screens it with the marker.

At this time, preferably, the normal pattern and the disease pattern are normalized with accumulated intensity at all the positions of the secondary ion masses (m/z), total accumulated intensity detected in a region where the secondary ion mass (m/z) is 1 to 500, or intensity of specific peaks, such as $CH_3^+$, configuring each pattern. When the normal pattern and the disease pattern are obtained by statistically processing the detection results of the plurality of secondary ion masses, the normalization is performed by an average of the accumulated intensity at all the positions of the secondary ion masses (m/z), an average of the total accumulated intensity detected in a region where the secondary ion mass (m/z) is 1 to 500, or an average of the intensity of the specific peaks, such as $CH_3^+$, configuring each pattern.

Specifically, after obtaining each pattern normalized with the intensity at all the positions of the secondary ion masses (m/z) of each pattern configured of the secondary ion mass (m/z) peaks, the average (a group of persons not having a disease and a group of patients having a disease, respectively) of the total accumulated intensity detected in the region where the secondary ion mass (m/z) is 1 to 500, or the average (a group of persons not having a disease and a group of patients having a disease, respectively) of the intensity of the specific peaks, such as $CH_3^+$, of the biological samples of persons not having a specific disease and the biological samples of patients having a specific disease the normal pattern and the disease pattern each pattern (normal pattern, disease pattern), it is preferable to extract the marker of the specific disease configured of the secondary ion mass (m/z) peaks having the large difference in the intensity through the statistical processing on the obtained patterns.

To minimize the effects of the measurement conditions of the time-of-flight secondary ion mass spectrometry and the preprocessing conditions of the biological samples and increase the accuracy of the marker screen, the normal pattern and the disease pattern is preferably obtained under the same measurement conditions of time-of-flight secondary ion mass spectrometry and the same preprocessing conditions of the biological samples and the different level of the intensity in the reference pattern and the object pattern can be obtained using the typical statistical algorithm.

A screening object secondary ion mass (m/z) region for extracting the marker judging the existence and non-existence of the disease is the region where the secondary ion mass (m/z) is 1 to 500, the secondary ion mass (m/z) region configuring the normal pattern and the secondary ion mass (m/z) region configuring the disease pattern are the same region, and the normal pattern and the disease pattern each is the pattern of the region where the secondary ion mass (m/z) is 1 to 500.

At this time, the normal pattern and the disease pattern also includes ones having the secondary ion not being detected at the position of the specific secondary ion mass of the constant secondary ion mass (m/z) regions.

The biological samples of the steps a) and b) may include excrements; urine; tears; salvia; external discharge of skin, respiratory tract, enteric tract, and digestive tract; plasma; serum; blood; spinal fluid; lymph; body fluid; tissue; tissue homogenate; portion of tissue; cell; cell extract; or in vitro cell culture.

Preferably, the disease is the large intestine cancer and the biological samples of the steps a) and b) are excrements or excremental liquid. Preferably, the excremental liquid is obtained by stirring excrements and buffer solution including phosphate buffered saline (PBS) and then separating the liquid.

In the case where the disease is the large intestine cancer, the marker extracted in the step c) is at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and is more preferably configured of at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass.

Most preferably, the extracted marker is configured of at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass normalized with the total accumulated intensity detected in the region where the secondary ion mass (m/z) is 1 to 500 or the intensity of the specific peak, such as $CH_3^+$.

The marker also includes ones (including the intensity of or the intensity of noise level) having ion not being detected at the position of the corresponding secondary ion mass.

A TOF-SIMS marker for judging a large intestine cancer according to the present invention is at least one secondary ion mass selected from a group of the following secondary ion masses (m/z) obtained by measuring excrements or excremental liquid by a time-of-flight secondary ion mass spectrometry (TOF-SIMS).

(TOF-SIMS Secondary Ion Mass)

81.0, 83.0, 125.9, 126.9, 131.9, 140.9, 141.9, 148.9, 157.9, 158.9, 205.1, 217.0, 222.9, and 233.0

Preferably, the TOF-SIMS marker for judging large intestine cancer is configured of at least one secondary ion mass selected from a group of secondary ion masses (m/z) of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass.

The TOF-SIMS marker for judging large intestine cancer extracts the different secondary ion masses and the intensity of the corresponding secondary ion masses by comparing a pattern not having large intestine cancer, which is a pattern configured of the secondary ion mass (m/z) peaks of excrements or excremental liquid of persons not having large intestine cancer, with a pattern having large intestine cancer, which is a pattern configured of the secondary ion mass (m/z) peaks of excrements or excremental liquid of patients having large intestine cancer.

Accordingly, the intensity of the secondary ion mass configuring the marker is the intensity of the corresponding secondary ion mass of the pattern not having large intestine cancer or the pattern having large intestine cancer, and specifically, is the intensity of 81.0, 83.0, 125.9, 126.9, 131.9, 140.9, 141.9, 148.9, 157.9, 158.9, 205.1, 217.0, 222.9, and 233.0 among the secondary ion masses (m/z) of the pattern not having large intestine cancer or the intensity of 81.0, 83.0, 125.9, 126.9, 131.9, 140.9, 141.9, 148.9, 157.9, 158.9, 205.1, 217.0, 222.9, and 233.0 among the secondary ion masses (m/z) of the pattern having large intestine cancer.

At this time, preferably, the intensity of the secondary ion mass configuring the marker is normalized with the total accumulated intensity (a group not having large intestine cancer and a group having large intestine cancer, respectively) of the region where the secondary ion mass (m/z) is 1 to 500 or the intensity (a group not having large intestine cancer and a group having large intestine cancer, respectively) of the specific peak.

When the pattern not having large intestine cancer or the pattern having large intestine cancer is obtained by statistically processing the detection results of the plurality of secondary ion masses, the normalization is performed by the average (a group not having large intestine cancer and a group having large intestine cancer, respectively) of the total accumulated intensity detected in the region where the secondary ion mass (m/z) is 1 to 500 or the average (a group not having large intestine cancer and a group having large intestine cancer, respectively) of the intensity of the specific peak, such as $CH_3^+$.

At this time, the excremental liquid is obtained by stirring excrements and buffer solution including phosphate buffered saline (PBS) and then separating the liquid.

A diagnosis method of a large intestine cancer according to the present invention diagnoses the large intestine cancer using a pattern of secondary ion mass (m/z) peaks of excrements or excremental liquid measured using a time-of-flight secondary ion mass spectrometry (TOF-SIMS) as the marker,.

Preferably, the excremental liquid is obtained by stirring excrements and buffer solution including phosphate buffered saline (PBS) and then separating the liquid. A solid-liquid separating for manufacturing the excremental liquid is performed using centrifugation.

Preferably, the pattern is a pattern where the secondary ion mass (m/z) is 1 to 500, wherein the pattern also includes ones having secondary ion not being detected at the position of the specific secondary ion mass in the region.

Preferably, the large intestine cancer is diagnosed by the change in the positions of the secondary ion mass peaks, the change in the intensity of the secondary ion mass peaks, the extinction of the secondary ion mass peaks, the generation of the secondary ion mass peaks, or a combination thereof by comparing at least one reference pattern selected from the pattern not having large intestine cancer being the pattern configured of the secondary ion mass peaks of the excrements or the excremental liquid of persons not having large intestine cancer and the pattern having large intestine cancer being the pattern configured of the secondary ion mass peaks of the excrements or the excremental liquid of patients having large intestine cancer with the object pattern being the pattern configured of the secondary ion mass peaks of the excrements or the excremental liquid of persons who can have large intestine cancer.

The reference pattern may be the pattern not having large intestine cancer or the pattern having large intestine cancer and is the pattern not having large intestine cancer and the pattern having large intestine cancer, and the similar level of the reference pattern and the object pattern can usually be performed using the typical statistical algorithm.

Preferably, the pattern not having large intestine cancer, the pattern having large intestine cancer, and the object pattern are normalized with the total accumulated intensity (a group not having large intestine cancer and a group having large intestine cancer, respectively) of the region where the secondary ion mass (m/z) is 1 to 500 or the intensity (a group not having large intestine cancer and a group having large intestine cancer, respectively) of the specific peak, such as $CH_3^+$.

At this time, the pattern not having large intestine cancer may be obtained by statistically processing at least one secondary ion mass pattern of persons not having large intestine cancer and the pattern having large intestine cancer may be obtained by statistically processing at least one secondary ion mass pattern of patients having large intestine cancer. In this case, each of the pattern not having large intestine cancer, the pattern having large intestine cancer, and the object pattern is normalized with the average of the total accumulated intensity of the region where the secondary ion mass (m/z) is 1 to 500 or the average of the intensity of the specific peak, such as $CH_3^+$.

Preferably, each of the pattern not having large intestine cancer, the pattern having large intestine cancer, and preferably, the object pattern is the pattern of the same secondary ion mass region of the region of 1 to 500 and is obtained under the measurement conditions of the same time-of-flight secondary ion mass spectrometry.

Preferably, the large intestine cancer is diagnosed by the similarity of the pattern through the comparison of the pattern not having large intestine cancer and/or the pattern having large intestine cancer. The similarity of the pattern is the same level of the generation position (m/z) configuring each pattern and the similarity of the relative intensity configuring each pattern, and when the pattern is similar to the pattern not having large intestine cancer, it is diagnosed to be the pattern not having large intestine cancer and when the pattern is similar to the pattern having large intestine cancer, it is diagnosed to be the pattern having large intestine cancer.

In the judgment of large intestine cancer, the comparison (the pattern being the marker of the disease) of the pattern not having large intestine cancer and/or the pattern having large intestine cancer with the object pattern is performed based on the intensity of at least one secondary ion mass selected from the group of the secondary ion masses of 81.0, 83.0, 125.9, 126.9, 131.9, 140.9, 141.9, 148.9, 157.9, 158.9, 205.1, 217.0, 222.9, and 233.0 and the intensity of the secondary ion mass.

More preferably, the pattern (the pattern being the marker) is configured of at least one secondary ion mass selected from the group of the secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding (selected) secondary ion mass normalized with the total accumulated intensity detected in the region where the secondary ion mass (m/z) is 1 to 500 or the intensity of the specific peaks, such as $CH_3^+$.

In detail, the intensity of the secondary ion mass of the pattern (the pattern being the marker) is the intensity of the corresponding secondary ion mass of the pattern not having large intestine cancer being the secondary ion mass (m/z) peaks of excrements or excremental liquid of persons not having large intestine cancer or the pattern having large intestine cancer being the secondary ion mass peak of excrements or excremental liquid of patients having large intestine cancer.

When judging the disease by selecting the plurality of secondary ion masses from the group of the secondary ion masses of 81.0, 83.0, 125.9, 126.9, 131.9, 140.9, 141.9, 148.9, 157.9, 158.9, 205.1, 217.0, 222.9, and 233.0, preferably, the disease is judged by the statistical detection tendency at the positions of the plurality of secondary ion masses selected from the group of the secondary ion masses configured of the 14 secondary ion masses (m/z).

Advantageous Effects

The diagnosis method using the TOF-SIMS of the present invention can rapidly, simply, and inexpensively diagnose a disease with a non-invasive method without giving patients a pain, has the high sensitivity and peculiarity of the diagnosis to early examine the disease, can be performed without the frequency of the examination, and has high accuracy.

The screening method using the TOF-SIMS of the present invention has an advantage of extracting a marker capable of diagnosing the existence and non-existence of the specific disease regardless of kinds of diseases by a simple method extracting the specific secondary ion mass having the difference between two groups by statistically processing the measuring spectrum of the group of persons not having a disease and the group of patients having a disease and has advantages of significantly reducing the time and costs required for extracting the marker.

The TOF-SIMS marker for diagnosing the disease of the present invention can rapidly, simply, and inexpensively diagnose a disease with a non-invasive method without giving patients a pain and is a stable marker not significantly affected by the preprocessing process of the sample, the measuring equipment for the TOF-SIMS, and the storage conditions of the sample.

DESCRIPTION OF DRAWINGS

The above and other objects, features and advantages of the present invention will become apparent from the following description of preferred embodiments given in conjunction with the accompanying drawings, in which:

FIG. 1 is a diagram arranging the test results on a group of persons not having a disease;

FIG. 2 shows a portion of a diagram arranging the test results on a group of patients having a disease;

FIG. 3 is a diagram continued to FIG. 2, wherein it shows a diagram showing the test results on a group of patients having a disease;

FIG. 5 is the test results on 20 excremental liquids belonging to a group of persons not having a disease, wherein it shows each of differences in the intensity detection results in a group of secondary ion masses extracted as a marker;

FIG. 7 is the results of a time-of-flight secondary ion mass spectrometry testing stability for hydrophilic property, wherein FIG. 7(a) is the results for excremental liquid extracted through phosphate buffered saline, FIG. 7(b) is the results for final excremental liquid removing lipid from the excremental liquid extracted through phosphate buffered saline using ethyl ether, FIG. 7(c) is the results for ethyl ether excrement extract, and FIG. 7(d) is results for ethyl ether itself.

FIG. 10A-C is a view showing the results performing a blind test on 54 excremental liquids belonging to a group of persons not having a disease and 47 excremental liquids belonging to a group of patients having a disease, wherein it shows each of the differences in the detection results in the group of the secondary ion masses extracted as the marker; and FIG. 11 is a view showing the blind test results using the TOF-SIMS marker and results performing a fecal occult blood testing (FOBT) on the same excrements used in the blind test.

BEST MODE

Figure 4:
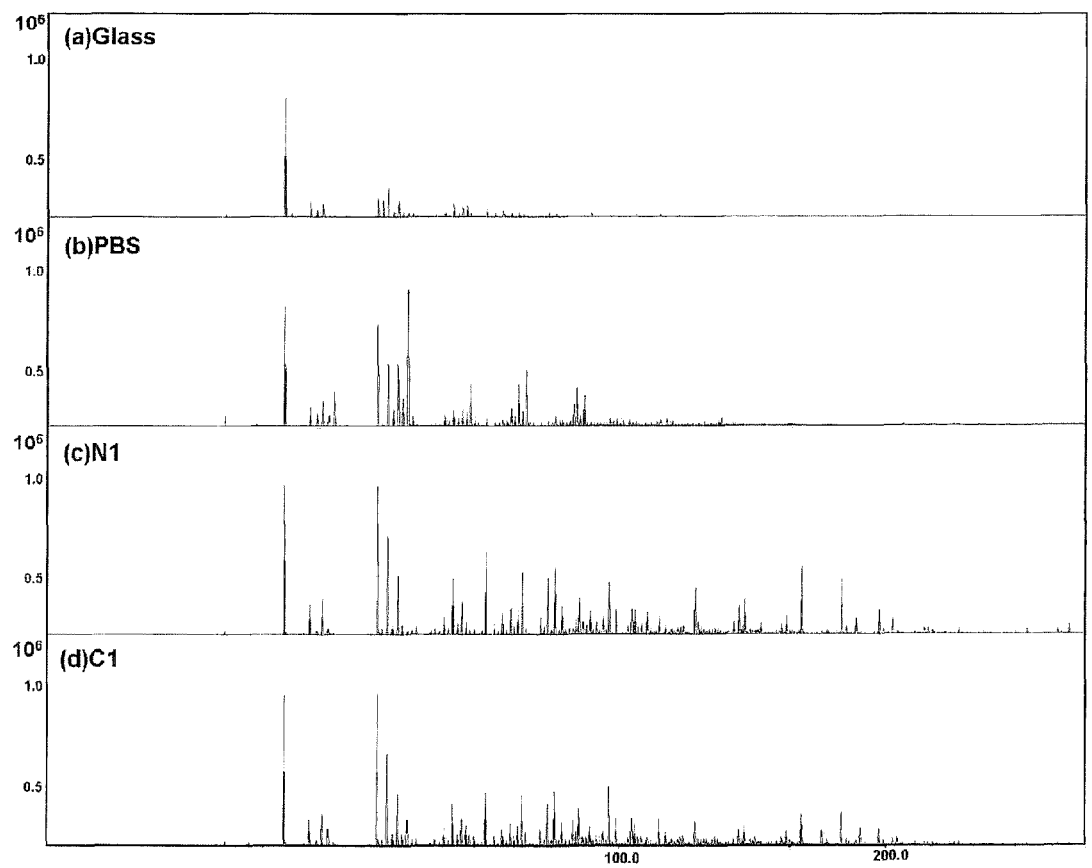
FIG. 4 is a view showing a glass substrate (FIG. 4(a)), phosphate buffered saline (FIG. 4b) including protease inhibitor used for harvesting excremental liquid, and results of a time-of-flight secondary ion mass spectrometry of a group of persons not having a disease (FIG. 4(c)) and a group of patients having a disease (FIG. 4(d))

The present applicant has been found from many experiments that a low mass region with secondary ion mass (m/z) of 500 or less, in particular, 300 or less is suitable for a marker capable of judging a disease, such as a cancer, in a disease diagnosis, a marker screening, and a TOF-SIMS marker capable of diagnosing a disease using a time-of-flight secondary ion mass spectrometry (TOF-SIMS).

The excellence of the present invention is experimentally proved by screening a marker of a large intestine cancer in the low mass region for the large intestine cancer as an object and extracting the TOF-SIMS marker for the large intestine cancer capable of diagnosing the large intestine cancer.

Hereinafter, a disease diagnosis method, a marker screening method, and a marker for a large intestine cancer as a diagnosis object according to the present invention will be described in detail. The following introduced embodiments are provided as an example to sufficiently transfer the concept of the present invention. Accordingly, the present invention is not limited to the embodiments, but can be embodied in other forms.

At this time, if technical and scientific terms used herein are not particularly defined, they have meanings understood by those skilled in the art. Hereinafter, a description for a related known function or configuration capable of making the gist of the present invention obscure will be omitted.

Marker Screening and Extracted Marker

Excrements of a group of 67 patients having a large intestine cancer and a group of 74 persons confirmed as not having a disease through a medical examination are harvested.

The group of 67 patients having large intestine cancer are subjected to a colonoscopy including a digital rectal examination, a blood test, a liver function test, a level of carcinoembryonic antigen (CEA), and a biopsy, a gastroscopy, a chest/abdomen and pelvis computed tomography (CT), a transrectal scanning (TRUS), a liver and pelvis magnetic resonance (MR) scanning, and an F-18 deoxyfluoroglucose positron emission tomography (FDGPET) test and are subjected to a test on a position and a progress stage of lesion.

The group of persons not having large intestine cancer, which are applicants participating in a health examination program of National Cancer Center, are proved as not having a disease through a colonoscopy including a digital rectal examination, a blood test, a liver function test, a level of carcinoembryonic antigen (CEA), and a biopsy, a gastroscopy, and a chest/abdomen and pelvis computed tomography (CT).

All the excrements harvested from the group of persons not having large intestine cancer and the group of patients having large intestine cancer are quantified by 10 g and stored at $-70°$ C. before their analysis. At this time, the excrements of the group of patients having large intestine cancer are harvested before an operation, an endoscopy, or a medical treatment for curing is performed on the patients.

FIG. 1 is a diagram arranging the test results on a group of persons not having a disease and FIGS. 2 and 3 shows a portion of a diagram arranging the test results on a group of patients having a disease.

In order to analyze the excrements harvested by the time-of-flight secondary ion mass spectrometry (hereinafter, referred to as "TOF-SIMS"), after mixing and stirring phosphate buffered saline (Roche Diagnostics Gmbh, Mannheim, Germany) including protease inhibitor and excrements, excremental liquid is separated using a centrifugal separator (12,000 g, 10 minutes). The excremental liquid obtained through the centrifugation drops on a glass slide, which is analyzed by the TOF-SIMS.

As measurement conditions of the TOF-SIMS, a TOF-SIMS V (ION-TOF GmbH, Germany) equipment mounted with a Bi ion gun is used. The equipment uses a 25 KeV $Bi_3^{++}$ ion gun and is operated in a high current bunched mode at 5 kHz at a pulse of 19.1 ns and its spatial resolution is several μm. The measuring region is 100×100 μm$^2$ and the amount of ions is maintained at 10$^{12}$ ionscm$^{-2}$ or less to satisfy static SIMS conditions. The measurement performed in positive and mass resolution (M/ΔM) is 7000 or more and a cation spectrum is calibrated using $CH_3^+$, $C_2H_3^+$, $C_3H_5^+$, and $C_7H_7^+$ peaks as a reference to obtain the accurate mass of the peaks. Also, the intensity of the peaks in all the secondary ion mass spectroscopy spectrums obtained through the measurement in the present embodiment is normalized with the total accumulated intensity up to 500 m/z or the intensity of $CH_3^+$.

FIG. 4 is a view showing a glass substrate (FIG. 4(a)), phosphate buffered saline (FIG. 4b) including protease inhibitor used for harvesting excremental liquid, and results of a time-of-flight secondary ion mass spectrometry of a group of persons not having a disease (FIG. 4(c)) and a group of patients having a disease (FIG. 4(d)). The measuring results of the excremental liquids belonging to each group are little difference.

The normalized TOF-SIMS of the group of persons not having a disease and the group of persons having a disease is statistically compared and analyzed. The upper 20 secondary ion mass peaks (P<0.05) showing a relatively large difference in the measuring results of each of the upper 20 groups of persons not having a disease and groups of persons not having a disease using a T-test are selected, the upper 20 secondary ion mass peaks is sorted and is classified into two groups using a k-NN(k-nearest neighbor, k=3) algorithm, and whether the classified results are actually classified into the group of persons not having a disease or the group of persons having a disease are confirmed through a leave-1-outcross validation (LOOCV) results. The secondary ion mass (m/z) of 13 (when being normalized with the total accumulated intensity up to 500 m/z, a group of secondary ion masses of m/z 81.0, 83.0, 125.9, 126.9, 140.9, 141.9, 148.9, 157.9, 158.9, 205.1, 217, 222.9, and 233.0) or 12 (when being normalized with the intensity of $CH_3^+$, a group of secondary ion masses of m/z 83.0, 125.9, 126.9, 131.9, 140.9, 141.9, 157.9, 158.9, 205.1, 217, 222.9, and 233.0), which can be the marker of the large intestine cancer, are extracted through the LOOCV results having the lowest receiver operation characteristic (ROC) error. The extracted secondary ion mass is statistically verified through a Fisher' exact test (P=5.8×10$^8$).

Figure 5:
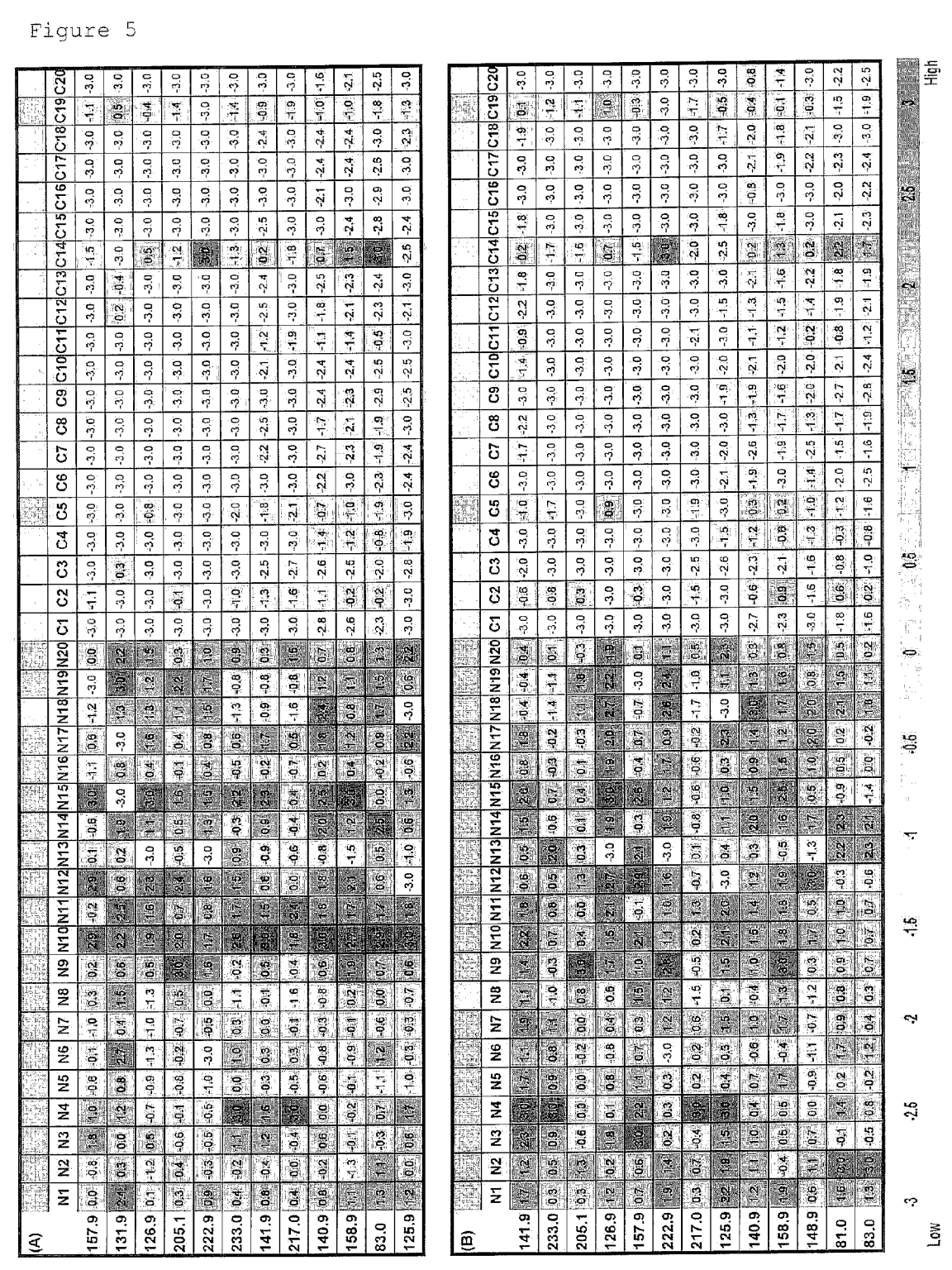

FIG. 5 is the test results on 20 excremental liquids belonging to a group of persons not having a disease, wherein it shows each of differences in intensity detection results in a group of secondary ion masses extracted as a marker and the decision results of an existence or non-existence of the large intestine cancer based on the LOOCV results. FIG. 5(a) are the results that uses the 12 secondary ion mass selected from the group of the secondary ion masses of 83.0, 125.9, 126.9, 131.9, 140.9, 141.9, 157.9, 158.9, 205.1, 217.0, 222.9, and 233.0 as the marker and are normalized with the intensity of $CH_3^+$ and FIG. 5(b) are the results that uses the 13 secondary ion mass selected from the group of the secondary ion masses of 81.0, 83.0, 125.9, 126.9, 140.9, 141.9, 148.9, 157.9, 158.9, 205.1, 217.0, 222.9, and 233.0 as the marker and are normalized with the total accumulated intensity of m/z 500 or less.

In FIG. 5, the relative intensity detected at the positions of each secondary ion mass being the marker is diagramed using a mathematical formula 1.

(Mathematical Formula 1)

Relative intensity of secondary ion mass (m/z) $X=$
$(X^{m/z}-X^{m/z}{\min})/(X^{m/z}{\max}-X^{m/z}{\min})\times 6-3$ At this time, $X^{m/z}$ is the intensity detected at the position of the m/z secondary ion mass of the specific sample, $X^{m/z}_{min}$ is the minimum intensity detected at the position of the m/z secondary ion mass, and $X^{m/z}_{max}$ is the maximum intensity detected at the position of the m/z secondary ion mass. At this time, $X^{m/z}$, $X^{m/z}_{min}$, and $X^{m/z}_{max}$ are the intensity normalized with the total accumulated intensity or the intensity of $CH_3^+$.

In FIG. 5, the detected intensity of each sample is shown by the aforementioned colors and numerical values. Therefore, as it approaches thick gray (+3), it means that the high intensity is detected and as it approaches white (-3), it means that the low intensity is detected.

In FIG. 5, N(N21-N20) is substantially a sample of excrements belonging to the group of persons not having a disease and C(C1-C20) is substantially a sample of excrements belonging to the group of persons having a disease, wherein the group of persons not having a disease and the group of persons having a disease classified (k-NN algorithm, classification using k=3) by the extracted marker are shown in the top partition of FIG. 5(a) and FIG. 5(b), and in the top partition, it means that the sample represented by black points in a square on a thick gray ground is classified into the group of persons having a disease and the sample represented by black points in a square on a white ground is classified into the group of persons not having a disease. The sensitivity and the peculiarity of the result TOF-SIMS large intestine cancer marker of the total 40 samples are 90% and 95%, respectively.

Through the aforementioned statistical method and the verification, the group of the secondary ion masses of 81.0, 83.0, 125.9, 126.9, 131.9, 140.9, 141.9, 148.9, 157.9, 158.9, 205.1, 217.0, 222.9, and 233.0 showing the high intensity in the group of persons not having a disease but showing the weak intensity or the peaks disappearing in the group of persons having a disease is extracted as the marker.

The group of all the extracted secondary ion masses can be used as the marker of the large intestine cancer, and preferably, at least one secondary ion mass selected from 81.0, 83.0, 125.9, 126.9, 131.9, 140.9, 141.9, 148.9, 157.9, 158.9, 205.1, 217, 222.9, and 233.0 not affected by the normalization method is used as the marker. However, the judgment of the existence or non-existence of a disease is performed by the statistical approach using a plurality of markers and therefore, the usable marker is not limited to the secondary ion mass not affected by the normalization method.

Figure 6:
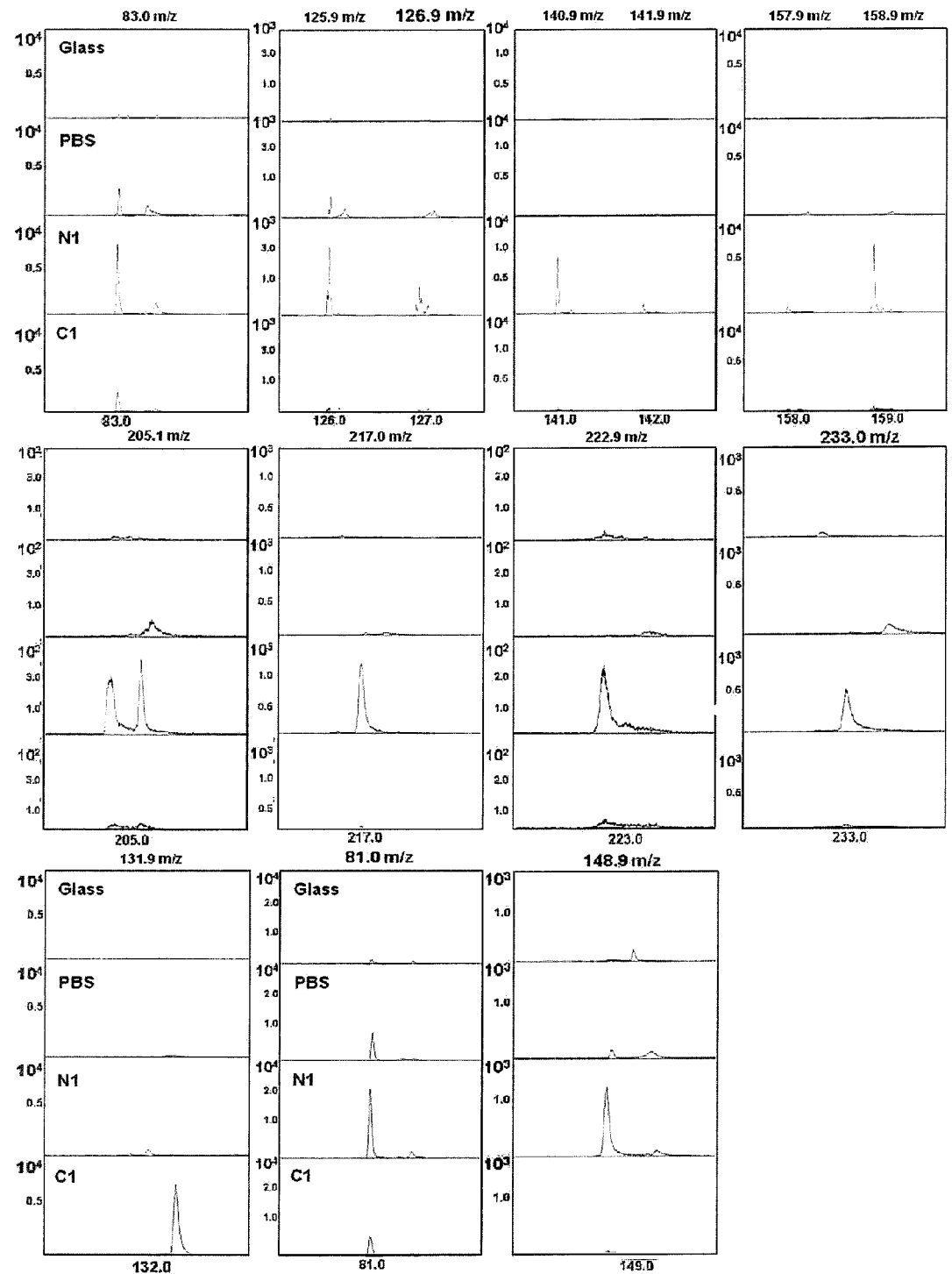
FIG. 6 is a view showing a difference in the detection results of a group of persons not having a disease (N1) and a group of patients having a disease (C1) in the group of the secondary ion masses extracted from a marker.

FIG. 6 is a view showing a difference in the detection results of the group of persons not having a disease (N1) and the group of patients having a disease (C1) in the group of the secondary ion masses extracted from the marker.

The stability for the hydrophilic property and heat of the extracted marker is tested. The extracted marker has the high intensity in the group of persons not having a disease and has the low intensity or does not indicate peaks in the group of persons having a disease so that the stability test is performed on the excrements of the group of persons not having a disease.

In the excrements of the group of persons not having a disease, after mixing/stirring the excremental liquid extracted through phosphate buffered saline with ethyl ether having the same volume, a process separating/removing the ethyl ether layer through the centrifugal separator (12,000 g, 5 minutes) is repeated twice to obtain the excrement extract where lipid is removed and the ethyl ether excrement extract, respectively.

Figure 7:
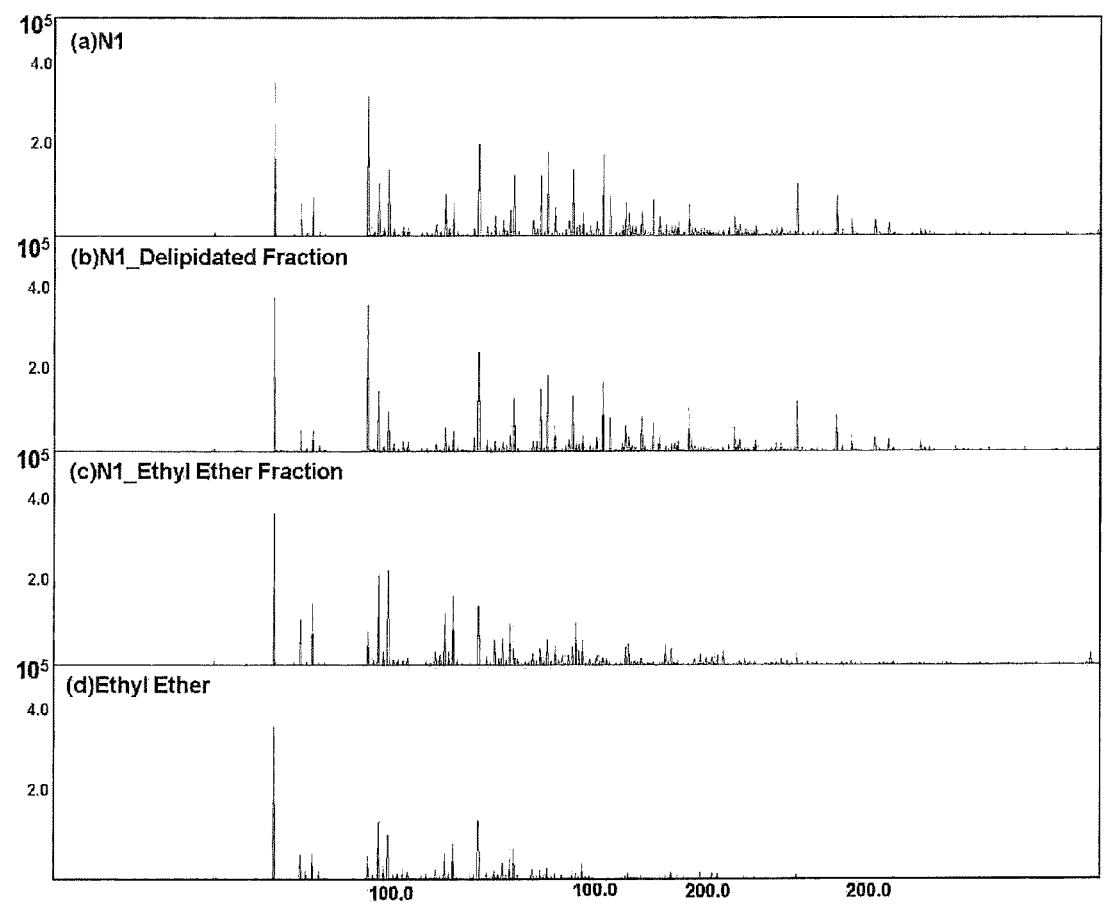

FIG. 7 is the results of the time-of-flight secondary ion mass spectrometry testing stability for hydrophilic property, wherein FIG. 7(a) is the results for excremental liquid extracted through the phosphate buffered saline, FIG. 7(b) is the results for the excremental extract removing lipid by adding ethyl ether to the excremental liquid extracted through the phosphate buffered saline, FIG. 7(c) is the results for ethyl ether excrement extract, and FIG. 7(d) is the results for ethyl ether itself.

Figure 8:
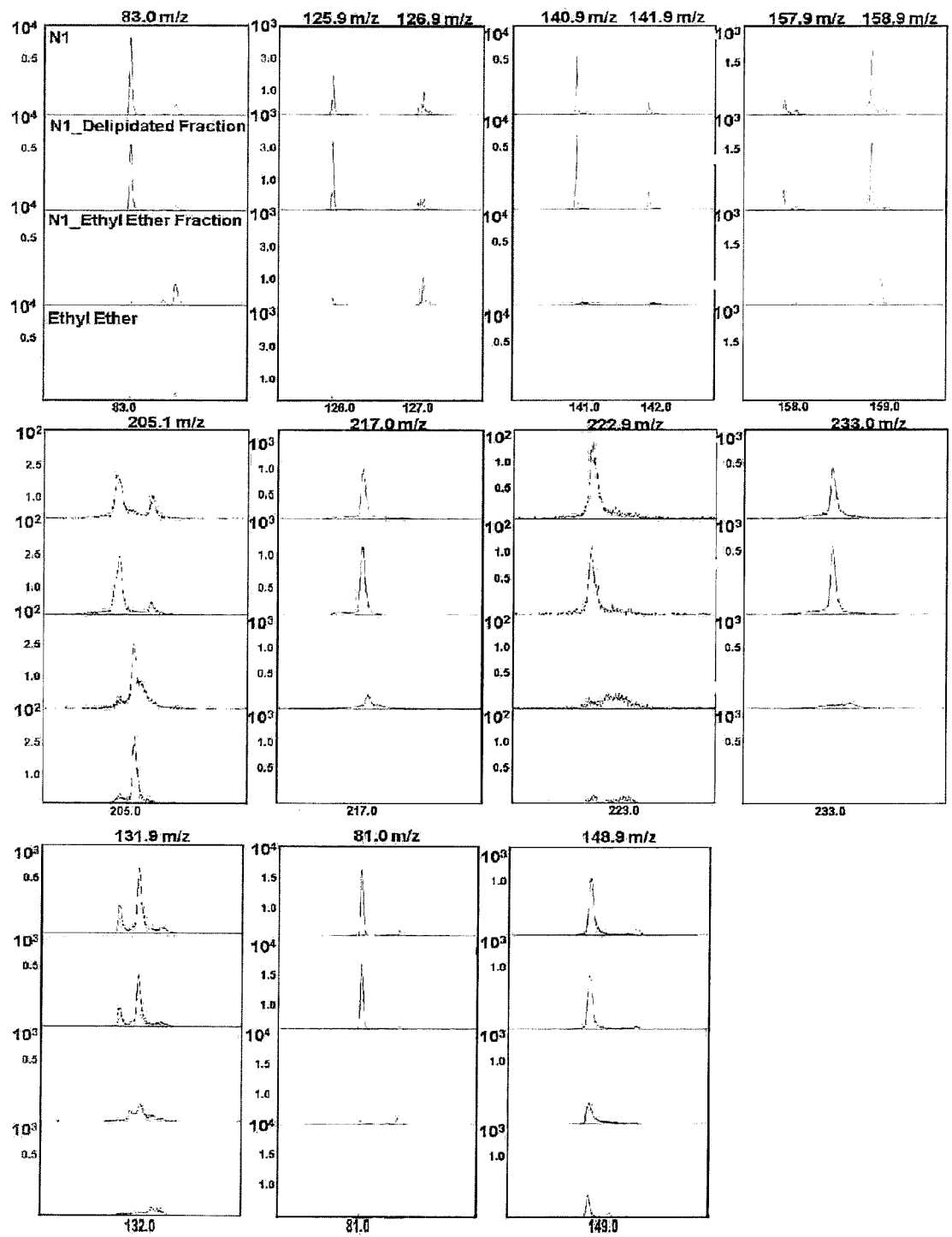
FIG. 8 is a view arranging stability for hydrophilic property of a group of secondary ion masses extracted as a marker.

FIG. 8 is a view arranging stability for hydrophilic property of the group of secondary ion masses extracted as a marker based on the FIG. 7.

Figure 9:
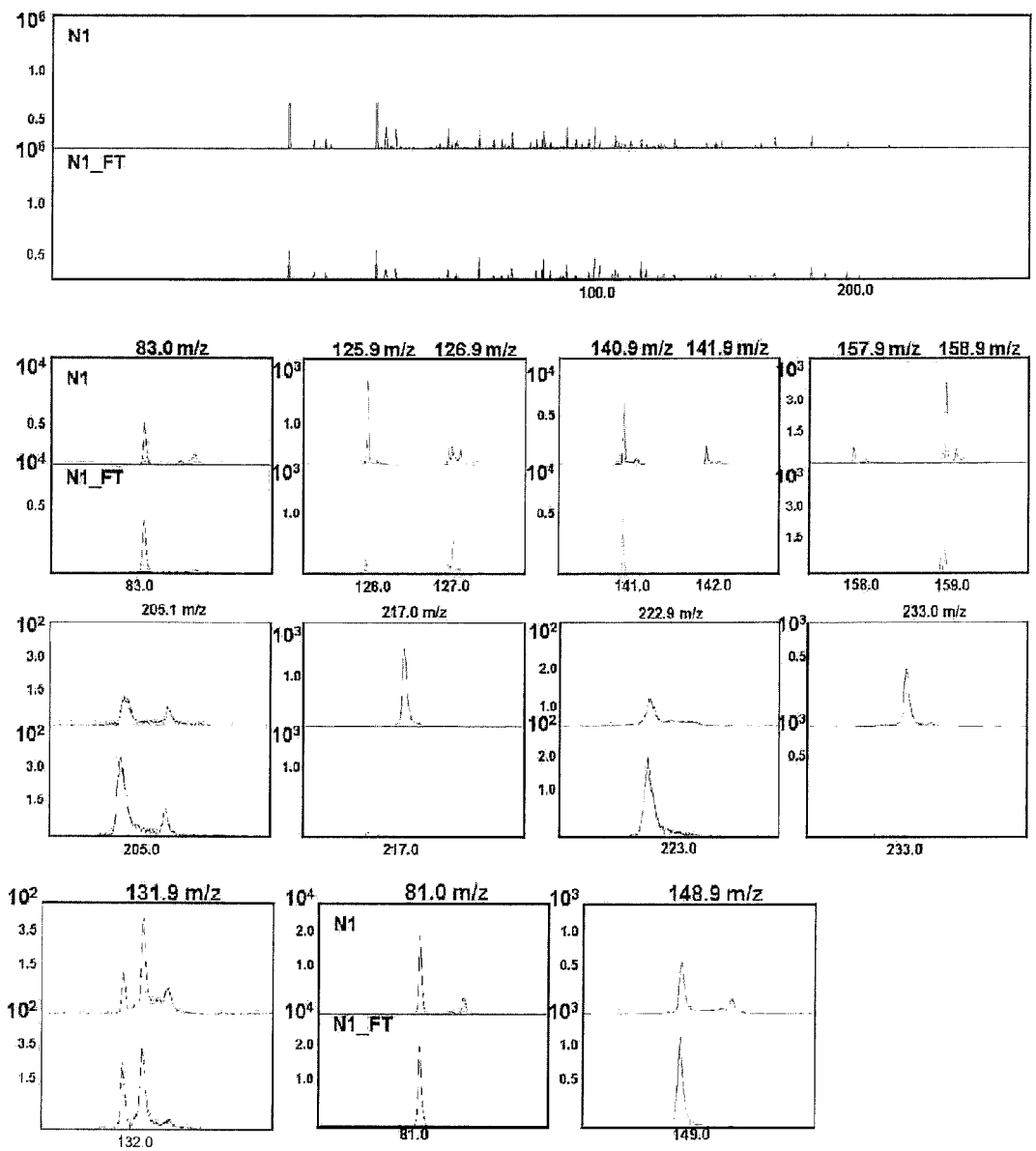
FIG. 9 is a view showing the results of a time-of-flight secondary ion mass spectrometry measured after freezing/melting excremental liquid extracted through phosphate buffered saline ten times.

FIG. 9 is a view showing the results (N1 of FIG. 9 is the results of the excremental liquid measured before the freezing/melting experiment and N1_FT of FIG. 9 is the results of the excremental liquid measured after the freezing/melting experiment) of the time-of-flight secondary ion mass spectrometry measured after freezing/melting excremental liquid extracted through the phosphate buffered saline ten times, wherein it can be appreciated that the degradation in the intensity occurs in the secondary ion mass (m/z) of 125.9, 141.9, 217.0, and 233.0 of the extracted markers, but the remaining markers are stabilized against the heat impact of the repeated freezing/melting. It can be appreciated from FIGS. 8 and 9 that the extracted marker is not changed according to the preprocessing of the sample and the storage conditions and therefore, is a very stable and reliable marker.

Blind Test Using Extracted Marker

The existence and non-existence of the large intestine cancer is diagnosed by the k-NN algorithm in the same conditions used in the extraction of the marker at the intensity detected in the secondary ion mass of 81.0, 83.0, 125.9, 126.9, 131.9, 140.9, 141.9, 148.9, 157.9, 158.9, 205.1, 217.0, 222.9, and 233.0 extracted as the marker.

The blind test is performed on the excrements used for the diagnosis of the large intestine cancer, which are the excrements belonging to the group of persons having large intestine cancer and the group of persons not having large intestine cancer used in the marker screening and extraction.

In the blind test, the preparation of the excremental liquid and the measurement conditions of the TOF-SIMS are the same as in the marker screening.

Figure 10A:
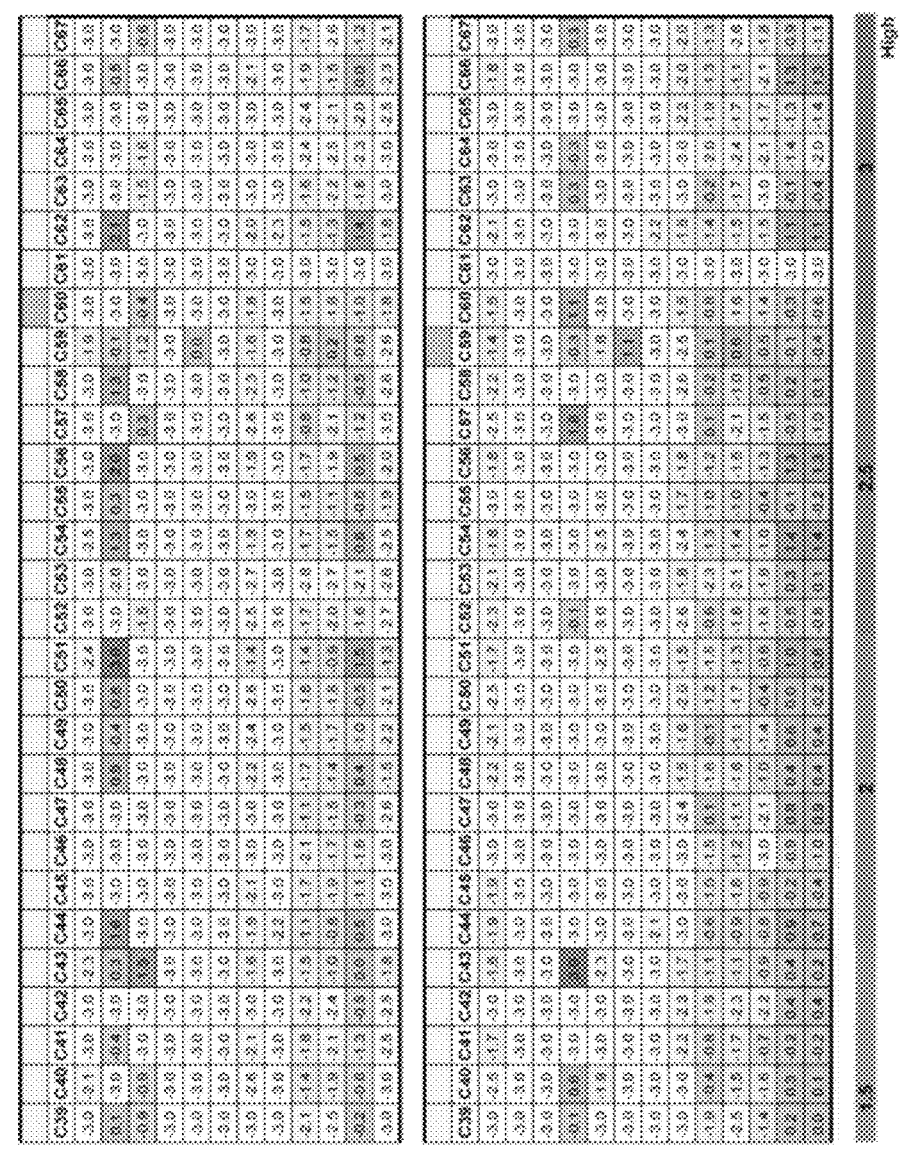
Figure 10B:
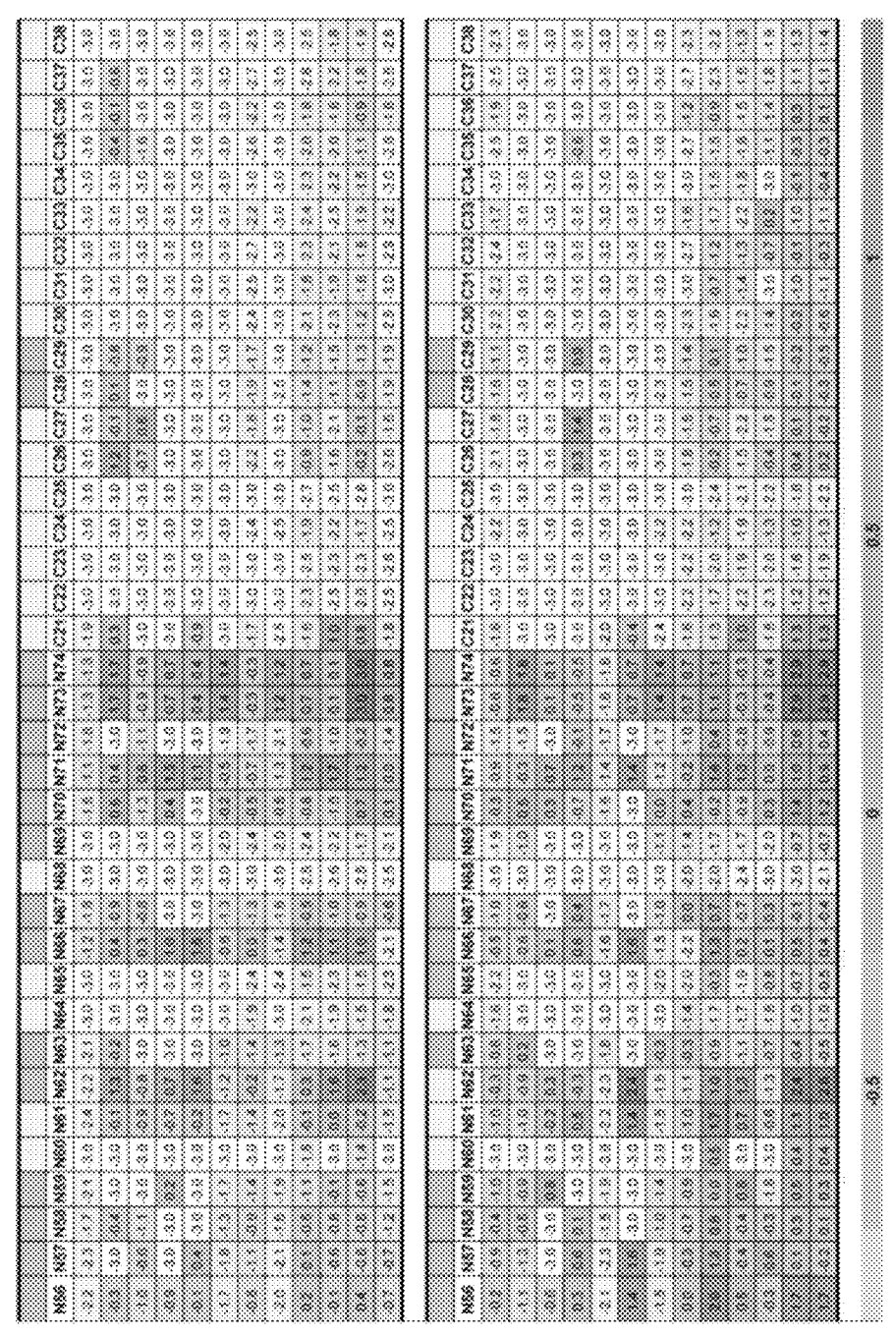
Figure 10C:
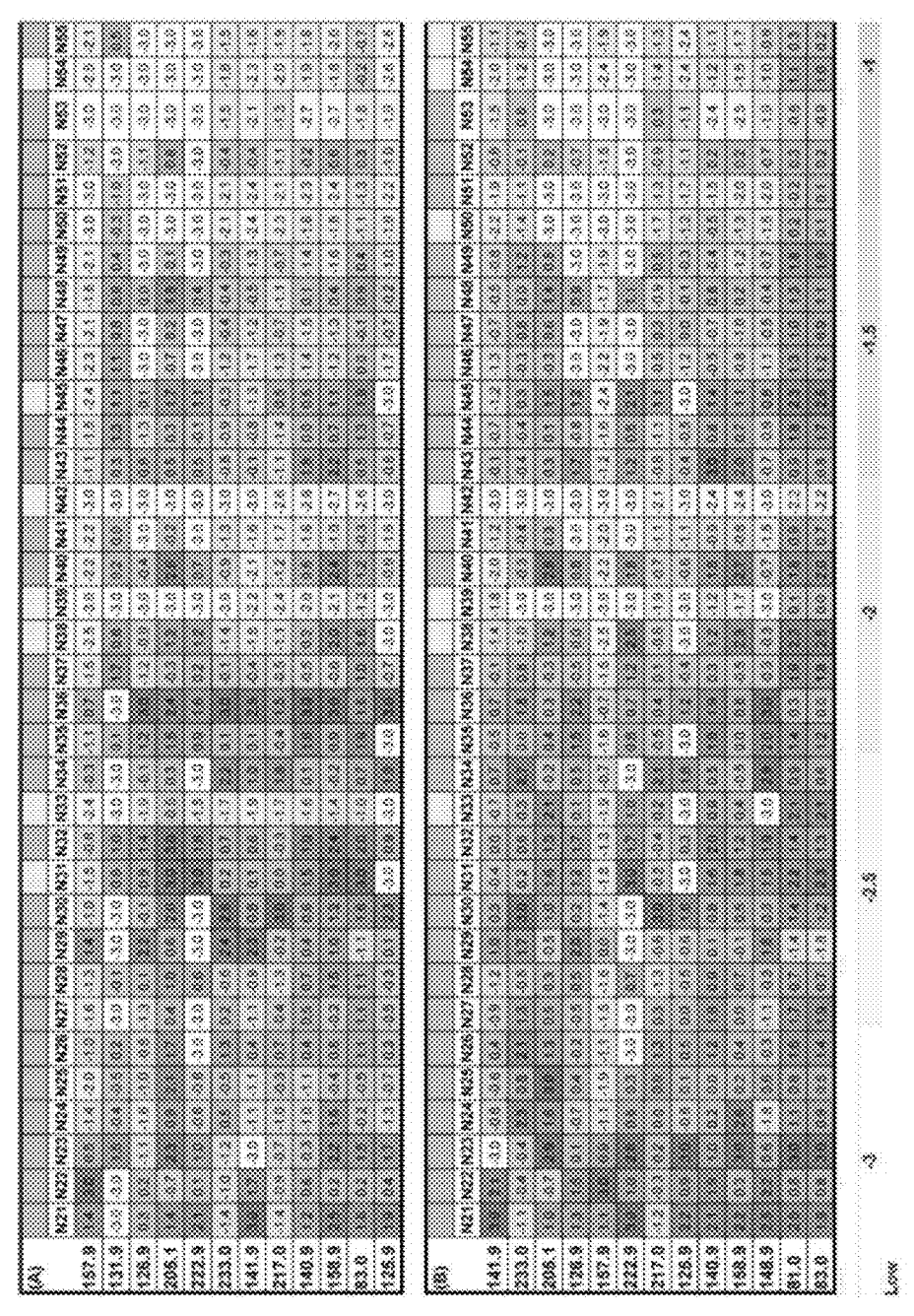

FIG. 10A-C is a view showing the results performing the blind test on 54 excremental liquids belonging to the group of persons not having a disease and 47 excremental liquids belonging to the group of patients having a disease, similarly to FIG. 5, wherein it shows the differences in the detection results in the group of the secondary ion masses extracted as the marker and the decision results of an existence or non-existence of the large intestine cancer based on the results detected by the k-NN algorithm, respectively. Similarly to FIG. 5, as it approaches thick gray (+3), it means that the high intensity is detected and as it approaches white (−3), it means that the low intensity is detected.

In FIG. 10A-C, the detected intensity of each sample is shown by the aforementioned colors and numerical values.

Likewise FIG. 5, FIG. 10C(A) is the results that uses the 12 secondary ion mass selected from the group of the secondary ion masses of 83.0, 125.9, 126.9, 131.9, 140.9, 141.9, 157.9, 158.9, 205.1, 217.0, 222.9, and 233.0 as the marker and are normalized with the intensity of $CH_3^+$ and FIG. 10C(B) are the results that uses the 13 secondary ion mass selected from the group of the secondary ion masses of 81.0, 83.0, 125.9, 126.9, 140.9, 141.9, 148.9, 157.9, 158.9, 205.1, 217.0, 222.9, and 233.0 as the marker and are normalized with the total accumulated intensity of m/z 500 or less, wherein the relative intensity detected at the positions of each secondary ion mass being the marker means that as it approaches white, the low intensity is detected. The judging results of the existence or non-existence of the large intestine cancer using the TOF-SIMS marker are shown in the top partition of FIG. 5(a) and FIG. 5(b), respectively, wherein in the top partition, it means that the sample represented by black points in a square on a thick gray ground is judged to be the group of persons having a disease and the sample represented by black points in a square on a white ground is judged to be the group of persons not having a disease. The sensitivity and the peculiarity of the blind test results on the total 101 samples are 93.6% and 77.8%, respectively.

FIG. 11 is a view arranging the blind test results (FIG. 10A-C) using the TOF-SIMS marker and the results performing a fecal occult blood testing (FOBT) on the same excrements used in the blind test. The fecal occult blood testing (FOBT) is performed using an OC sensor kit (EIKEN Chemical Co. Ltd., Tokyo, Japan), wherein a reference of positive reaction is 100 ng Hb/ml.

In FIG. 11, the "total intensity" is a case where the measured TOF-SIMS spectrum is normalized with the total accumulated intensity of m/z 500 or less and "$CH_3^+$" is a case normalized with the intensity of $CH_3^+$. Also, N means that the test results through the TOF-SIMS marker are judged to be normal and C means that the test results through the TOF-SIMS marker is judged to be the large intestine cancer. The control and the patient substantially mean the excrements belonging to the group of persons not having large intestine cancer and the group of persons having large intestine cancer.

As can be appreciated from the results of FIG. 11, the normalization method of the TOF-SIMS spectrum has little effect on the sensitivity and the peculiarity of the extracted marker, and it can be appreciated that according to the diagnosis results using the TOF-SIMS, the sensitivity and the peculiarity are 93.6% and 77.8%, while in the case of the fecal occult blood testing, the positive reaction is indicated only in 37 excrements of the excrements of patients having large intestine cancer (sensitivity 63.8%, peculiarity 100%).

[Industrial Applicability]

The diagnosis method using the TOF-SIMS of the present invention can rapidly, simply, and inexpensively diagnose a disease with a non-invasive method without giving patients a pain, has the high sensitivity and peculiarity of the diagnosis to early examine the disease, can be performed without the frequency of the examination, and has high accuracy.

The screening method using the TOF-SIMS of the present invention has an advantage of extracting a marker capable of diagnosing the existence and non-existence of the specific disease regardless of kinds of diseases by a simple method extracting the specific secondary ion mass having the difference between two groups by statistically processing the measuring spectrum of the group of persons not having a disease and the group of patients having a disease and has advantages of significantly reducing the time and costs required for extracting the marker.

The TOF-SIMS marker for diagnosing the disease of the present invention can rapidly, simply, and inexpensively diagnose a disease with a non-invasive method without giving patients a pain and is a stable marker not significantly affected by the preprocessing process of the sample, the measuring equipment for the TOF-SIMS, and the storage conditions of the sample.

The invention claimed is:

1. A marker screening method using a TOF-SIMS comprising the steps of:
   a) obtaining a normal pattern being a pattern configured of secondary ion mass (m/z) peaks of biological samples of persons not having a specific disease;
   b) obtaining a disease pattern being a pattern configured of secondary ion mass (m/z) peaks of biological samples of patients having a specific disease; and c) extracting a marker of a specific disease by comparing the difference in the normal pattern and the disease pattern.

2. The marker screening method according to claim 1, wherein the step c) extracts at least one secondary ion mass (m/z) selected from a group of the position changed, intensity changed, extinct, and generated peaks by comparing the normal pattern and the disease pattern.

3. The marker screening method according to claim 1, wherein each of the normal pattern and the disease pattern is normalized with total accumulated intensity in a region where the secondary ion mass (m/z) is 1 to 500 or intensity of specific peak.

4. The marker screening method according to claim 3, wherein each of the normal pattern and the disease pattern is a pattern in a region where the secondary ion mass (m/z) is 1 to 500.

5. The marker screening method according to claim 1, wherein the biological samples of the steps a) and b) may include excrements; urine; tears; salvia; external discharge of skin, respiratory tract, enteric tract, and digestive tract; plasma; serum; blood; spinal fluid; lymph; body fluid; tissue; tissue homogenate; portion of tissue; cell; cell extract; or in vitro cell culture.

6. The marker screening method according to claim 5, wherein the disease is a large intestine cancer.

7. The marker screening method according to claim 6, wherein the biological samples of the steps a) and b) are excrements or excremental liquid.

8. The marker screening method according to claim 6, wherein in the step c) the extracted marker is configured of at least one secondary ion mass selected from a group of secondary ion masses of 81.0, 83.0, 125.9, 126.9, 131.9, 140.9, 141.9, 148.9, 157.9, 158.9, 205.1, 217.0, 222.9, and 233.0 and the intensity of the corresponding secondary ion mass.

* * * * *